(12) United States Patent
Brown, Jr. et al.

(10) Patent No.: US 8,166,601 B2
(45) Date of Patent: May 1, 2012

(54) ELECTRIC TOOTHBRUSH HEAD

(75) Inventors: William R. Brown, Jr., Peabody, MA (US); Thomas Christman, Lexington, MA (US); Georges Driesen, Weilrod (DE); Thomas Fritsch, Eppstein (DE); Michael Roberts, Brookfield, CT (US); Armin Schwarz-Hartmann, Wendelsheim (DE)

(73) Assignee: Braun GmbH, Kronberg (DE)

( * ) Notice: Subject to any disclaimer, the term of this patent is extended or adjusted under 35 U.S.C. 154(b) by 411 days.

(21) Appl. No.: 12/008,774

(22) Filed: Jan. 14, 2008

(65) Prior Publication Data
US 2008/0172814 A1 Jul. 24, 2008

Related U.S. Application Data

(63) Continuation of application No. 11/513,632, filed on Aug. 31, 2006, now abandoned, which is a continuation of application No. 09/824,310, filed on Apr. 2, 2001, now abandoned.

(51) Int. Cl.
*A46B 9/04* (2006.01)
(52) U.S. Cl. ......................................... 15/201; 15/167.1
(58) Field of Classification Search ........... 15/28, 167.1, 15/201
See application file for complete search history.

(56) References Cited

U.S. PATENT DOCUMENTS

| 1,901,230 | A |   | 3/1933  | Duey |
|-----------|---|---|---------|------|
| 2,155,245 | A |   | 4/1939  | Ioki |
| 2,706,825 | A | * | 4/1955  | Blakeman ............... 15/176.4 |
| 2,935,755 | A |   | 5/1960  | Leira et al. |
| 3,129,449 | A |   | 4/1964  | Cyzer |
| 4,694,844 | A |   | 9/1987  | Berl et al. |
| 4,776,054 | A |   | 10/1988 | Rauch |
| 5,046,213 | A |   | 9/1991  | Curtis et al. |
| D329,946  | S |   | 10/1992 | Curtis et al. |
| D334,288  | S |   | 3/1993  | Witzig-Jaggi |
| D343,294  | S |   | 1/1994  | Curtis et al. |
| 5,325,560 | A | * | 7/1994  | Pavone et al. ................ 15/106 |
| 5,335,389 | A |   | 8/1994  | Curtis et al. |
| 5,392,483 | A |   | 2/1995  | Heinzelman et al. |
| 5,467,495 | A | * | 11/1995 | Boland et al. .................. 15/28 |
| D364,740  | S |   | 12/1995 | Loew |
| 5,500,970 | A |   | 3/1996  | Maurer et al. |

(Continued)

FOREIGN PATENT DOCUMENTS
DE 2461055 7/1976
(Continued)

*Primary Examiner* — Laura C Guidotti
(74) *Attorney, Agent, or Firm* — George H. Leal; John P. Colbert

(57) ABSTRACT

A head for an electric toothbrush includes a support member having a plurality of holes extending completely therethrough. A plurality of tufts of bristles each extends through one of the holes. A first brushing end of each tuft projects from a first side of the support member. Each tuft is prevented from being withdrawn from its hole when a tensile force is applied to the first end of each tuft along a long axis of the tuft. A resilient cushion is positioned adjacent a second side of the support member such that a second end of each tuft can contact the cushion. When a compressive force is applied to the first end of each tuft along the long axis of each tuft, each tuft can move in its hole in a first direction into the cushion. When the compressive force is removed the cushion causes each tuft to move in its hole in a second direction substantially opposite the first direction.

11 Claims, 5 Drawing Sheets

U.S. PATENT DOCUMENTS

| | | | |
|---|---|---|---|
| D370,347 S | 6/1996 | Heinzelman et al. | |
| 5,524,319 A * | 6/1996 | Avidor | 15/167.1 |
| 5,628,082 A * | 5/1997 | Moskovich | 15/110 |
| 5,689,850 A | 11/1997 | Shekalilm | |
| D387,206 S | 12/1997 | Yammamoto et al. | |
| 5,802,656 A | 9/1998 | Dawson et al. | |
| D402,114 S | 12/1998 | Fleming et al. | |
| D402,116 S | 12/1998 | Magloff et al. | |
| D402,117 S | 12/1998 | Fleming et al. | |
| D403,510 S | 1/1999 | Menke et al. | |
| 5,875,510 A | 3/1999 | Lamond et al. | |
| 5,896,614 A | 4/1999 | Flewitt | |
| 6,016,587 A | 1/2000 | Savitt et al. | |
| 6,021,538 A | 2/2000 | Kressner et al. | |
| D434,565 S | 12/2000 | Bojar | |
| D437,688 S | 2/2001 | Beals et al. | |
| 6,308,367 B1 | 10/2001 | Beals et al. | |
| 6,363,565 B1 | 4/2002 | Paffrath | |
| D456,607 S | 5/2002 | Carlucci et al. | |
| 6,553,604 B1 * | 4/2003 | Braun et al. | 15/167.1 |

FOREIGN PATENT DOCUMENTS

| | | |
|---|---|---|
| DE | 2652744 | 6/1977 |
| DE | 8807968 | 10/1989 |
| DE | 3937850 | 5/1991 |
| EP | 0449655 | 10/1991 |
| EP | 0765642 | 6/1996 |
| WO | WO 97/03587 | 2/1997 |
| WO | WO 00/21406 | 4/2000 |
| WO | WO 01/14117 | 3/2001 |

* cited by examiner

ELECTRIC TOOTHBRUSH HEAD

CROSS-REFERENCE TO RELATED APPLICATIONS

This application is a continuation of application Ser. No. 11/513,632 filed on Aug. 31, 2006 now abandoned which is a continuation of application Ser. No. 09/824,310 filed on Apr. 2, 2001 now abandoned, each of which is incorporated herein by reference.

FIELD OF THE INVENTION

The invention relates generally to the field of oral care, and in particular to toothbrushes. More specifically, the invention relates to electric toothbrushes.

BACKGROUND OF THE INVENTION

Electric toothbrushes are well known and have been on the market for years. With typical electric brushes all of the tufts of bristles on the brush head are vertically oriented relative to the top surface of the head. The tufts are oscillated, rotated and/or translated in order to provide enhanced tooth cleaning capability.

German Gebrauchsmuster 8807968.6 discloses a head for an electric toothbrush. A first group of circular tufts 18 are arrayed in a first ring about the center of rotation of the head. A second group of taller circular tufts 16 are arrayed in a second ring which is outside the first ring and also encircles the center of rotation of the head. All of tufts 16 and 18 are circular in cross-section and are canted away from the center of the head at an acute angle relative to a top surface of the head A problem with this brush is that all of the tufts have a circular cross-section. Such tufts are not that effective at penetrating between teeth to clean the interdental or approximal areas of the teeth. Further, all but one of the tufts are angled away from the center. Such a tuft pattern tends to flair (flatten) out even more than designed during use, thereby having the same brushing characteristics as a worn-out standard brush. Additionally, none of the tufts are angled along the direction of the rotational circumference which results in even poorer interdental penetration of the bristles.

European Patent 0765642 also discloses a head for an electric toothbrush. There are a number of bristle tufts 17 which are vertically oriented on the head. Bristle tufts 13, 15 are located about a perimeter of the circular head and are tilted at an acute angle along a circumference of a top surface of the head. All of the tufts on the head have a circular cross-section.

Again we see the problem of a brush head in which all of the tufts have a circular-cross-section: such tufts do not penetrate well in the approximal tooth areas. This head also has no tufts which are angled away from the center to sweep along the gum line or gingival margin of the mouth. Further, in two pairs of the tufts 13, the tufts are adjacent to each other and are angled towards each other. These two tufts appear to be in contact. A downside to this tuft arrangement is that the two adjacent tufts can tend to interfere with each other during use of the brush. In addition, due to the tuft configuration and shape, a lot of the available space of the head is not used. This reduces efficacy and increases wear of the head (flare) upon use. For effective brushing approximately 32-36% of the head surface must be covered with tufts/bristles.

SUMMARY OF THE INVENTION

The present invention may overcome one or more of the problems set forth above. Briefly summarized, according to one aspect of the present invention, a head for an electric toothbrush includes a support member and a plurality of tufts of bristles supported at their base by the support member. Two of the tufts have their bases adjacent to each other and are tilted away from each other at an acute angle relative to the support member.

According to a second aspect of the invention, a head for an electric toothbrush includes a support member having a plurality of holes extending completely therethrough. A plurality of tufts of bristles each extends through one of the holes. A first brushing end of each tuft projects from a first side of the support member. Each tuft is prevented from being withdrawn from its hole when a tensile force is applied to the first end of each tuft along a long axis of the tuft. A resilient cushion is positioned adjacent a second side of the support member such that a second end of each tuft can contact the cushion. When a compressive force is applied to the first end of each tuft along the long axis of each tuft, each tuft can move in its hole in a first direction into the cushion. When the compressive force is removed the cushion causes each tuft to move in its hole in a second direction substantially opposite the first direction.

According to a third aspect of the invention, a head for an electric toothbrush includes a support member and a plurality of tufts of bristles supported at their base by the support member. The support member has a substantially circular surface from which the tufts project. A first one of the tufts is tilted along an imaginary radius which projects from a center of the circular surface and passes through a base of the first tuft. A second one of the tufts is tilted along an imaginary circumference which encircles the center of the circular surface and passes through a base of the second tuft.

According to a fourth aspect of the invention, a head for an electric toothbrush includes a support member and a plurality of tufts of bristles supported at their base by the support member A pair of the tufts is tilted in substantially the same direction relative to the support member. A first tuft of the pair has a different cross-section than a second tuft of the pair.

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Figure 1:
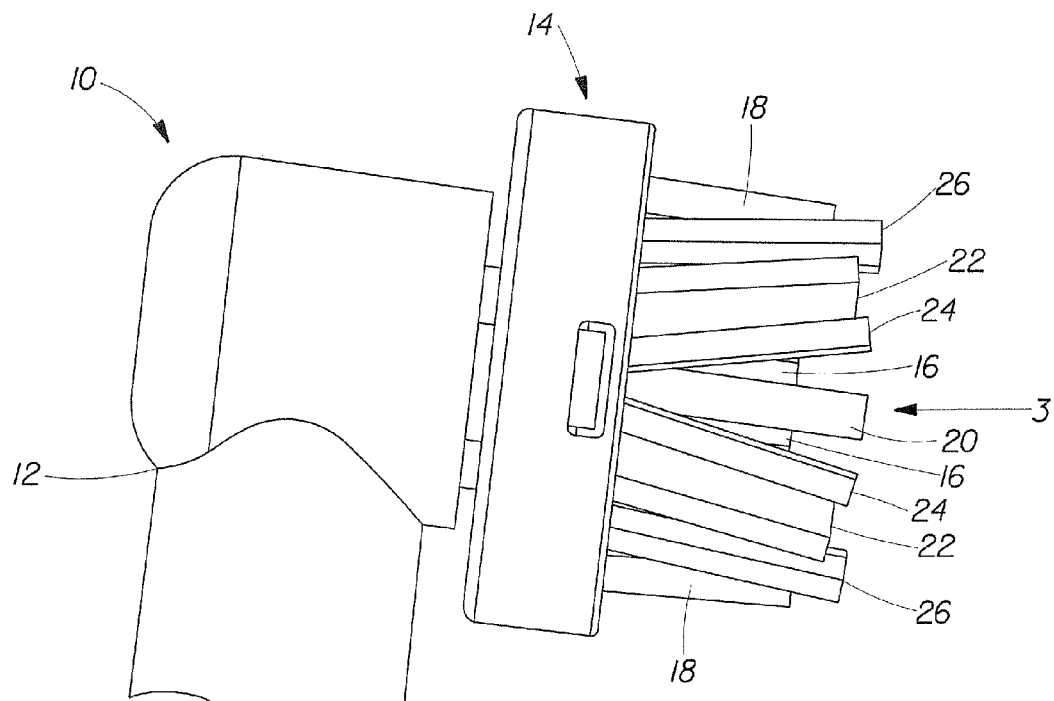
FIG. 1 is a side view of a portion of an electric toothbrush.
Figure 3:
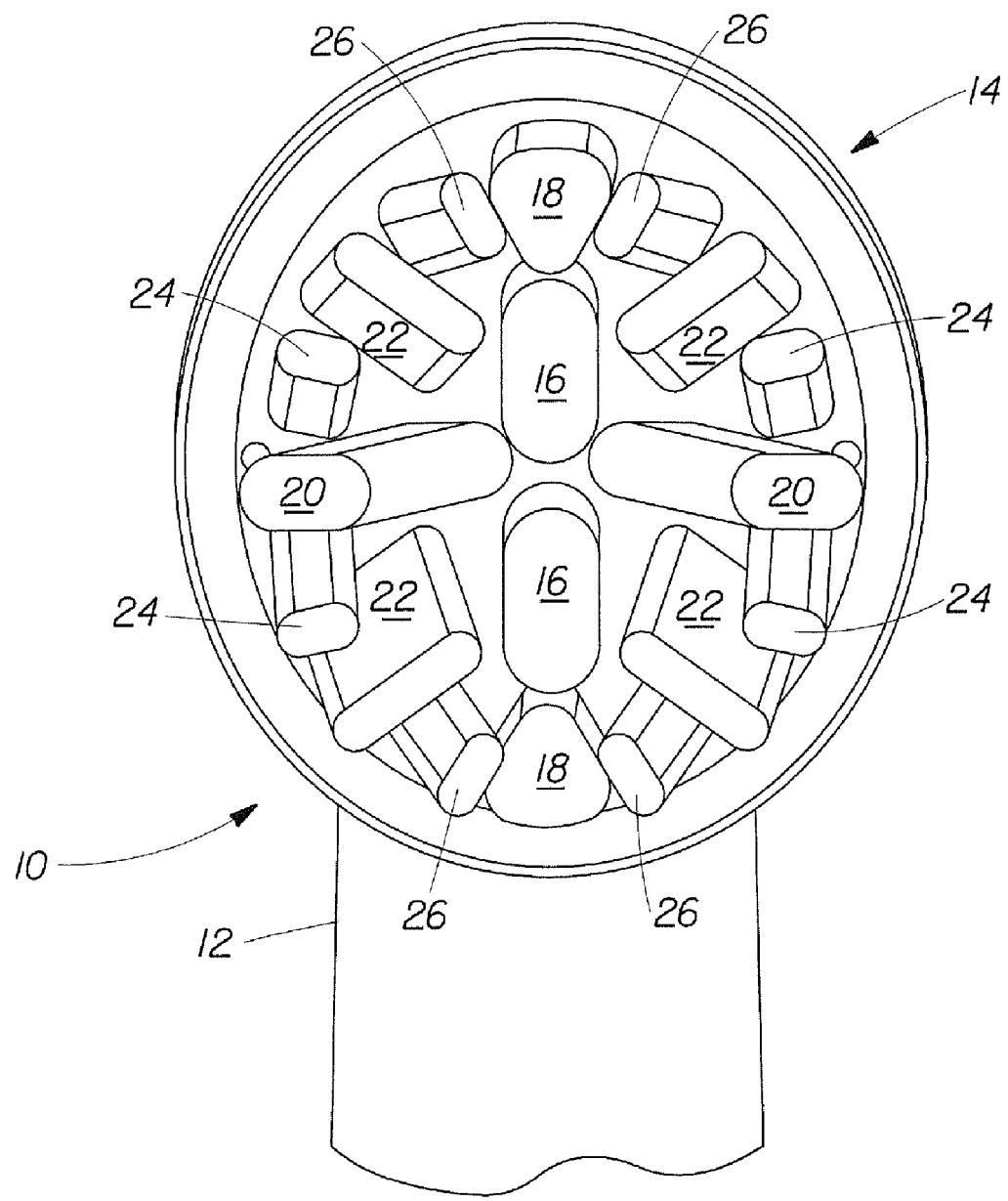
FIG. 3 is a front view of FIG. 1 looking along the direction of arrow 3.

Embodiment 1
Beginning with FIGS. 1 and 3, an electric toothbrush 10 includes a neck 12 and a head 14. As is well known to those skilled in the art, head 14 is oscillated through an angle of preferably +−20 to 50 degrees about an axis parallel to an arrow 3. Electrical power is preferably supplied by rechargeable or single use batteries. The batteries power an electric motor which, through gearing or another linking element, oscillates the head. Further details as to how the head is oscillated will not be provided as this aspect of the brush is not the focus of the invention.

Head 14 contains a large number of tufts of varying lengths, cross-sections and orientations. Although each tuft is shown as a solid mass in the drawings, the tufts are actually each made up of a great mass of individual plastic bristles. The bristles are preferably made of 612 nylon. Each of tufts 16 are oval in cross-section with a 6.1 mm height. The dimensions of the oval are 1.78 mm×3.05 mm. 5 or 6 mil filament can be used for tuft 16. The tuft is vertically oriented relative to the top surface of the head.

Each of tufts 18 are triangular in cross-section with rounded vertexes (tri-oval in shape). These tufts are 6.35 mm in height with a dimension of 2.03 mm from the rounded vertex nearest the center of the head to its opposite side. Tufts 18 also have a dimension of 2.28 mm between the two remaining rounded vertices. Preferably 6 mil filament is used to make the bristles for this tuft. The tuft is vertically oriented relative to the top surface of the head.

Each of tufts 20 are oval in cross-section with a 7.62 mm height. The dimensions of the oval are 1.27 mm×2.28 mm. 6 mil filament can be used for tufts 20. The tuft is tilted away from the center of the head at an angle of about 20 degrees relative to the top surface of the head. The long dimension of the oval cross-section lies along the direction of tilt of tuft 20.

Each of tufts 22 are oval in cross-section with a 7.37 mm height. The dimensions of the oval are 0.76 mm×3.05 mm. 6 mil filament can be used for tufts 22. The tuft is tilted along an imaginary circular line whose center is concentric with the head's center. The angle of tilt is about 20 degrees relative to the top surface of the head. The long dimension of the oval cross-section is aligned substantially towards the center of the head.

Each of tufts 24 are oval in cross-section with a 7.62 mm height. The dimensions of the oval are 0.76 mm×1.52 mm. 6 mil filament can be used for tufts 22. The tuft is tilted along an imaginary circular line whose center is concentric with the head's center. The angle of tilt is about 12 degrees relative to the top surface of the head. The long dimension of the oval cross-section is aligned substantially towards the center of the head.

Each of tufts 24 are oval in cross-section with a 7.62 mm height. The dimensions of the oval are 0.76 mm×1.52 mm. 6 mil filament can be used for tufts 22. The tuft is tilted along an imaginary circular line whose center is concentric with the head's center. The angle of tilt is about 12 degrees relative to the top surface of the head. The long dimension of the oval cross-section is aligned substantially towards the center of the head.

Each of tufts 26 are oval in cross-section with a 8.4 mm height. The dimensions of the oval are 0.76 mm×1.52 mm. 6 mil filament can be used for tufts 22. The tuft is tilted along an imaginary circular line whose center is concentric with the head's center. The angle of tilt is about 12 degrees relative to the top surface of the head. The long dimension of the oval cross-section is aligned substantially towards the center of the head.

Figure 2:
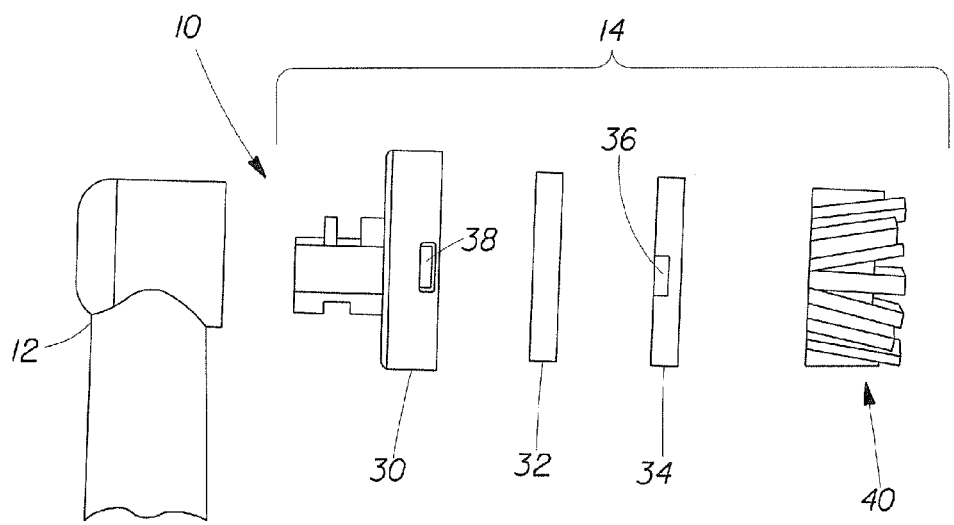
FIG. 2 is a is an exploded view of FIG. 1.

Turning now to FIG. 2, a more detailed description of head 14 will be provided. A plastic base member 30 is supported in neck 12 and is driven by gearing or another driving element (not shown) to oscillate the head. A resilient cushion 32 is made of a thermoplastic elastomer and is positioned within base member 30. A plastic support member 34 has a number of wholes therethrough which match in number and shape the number and shape of all of the tufts of bristles. Base member and support member can be made of Delrin. Cushion 32 can be made of GLS Dynaflex G 6703

A pair of catches 36 (only one is visible) in support member 34 engage a pair of openings 38 in base member 30 to secure the support member to the base member in a snap-fit arrangement which securely traps cushion 32 therebetween. Tufts 40 are supported at their bases by the support member. The lower portions of the tufts are not shown in FIG. 2 but will be described in further detail below.

Figure 4:
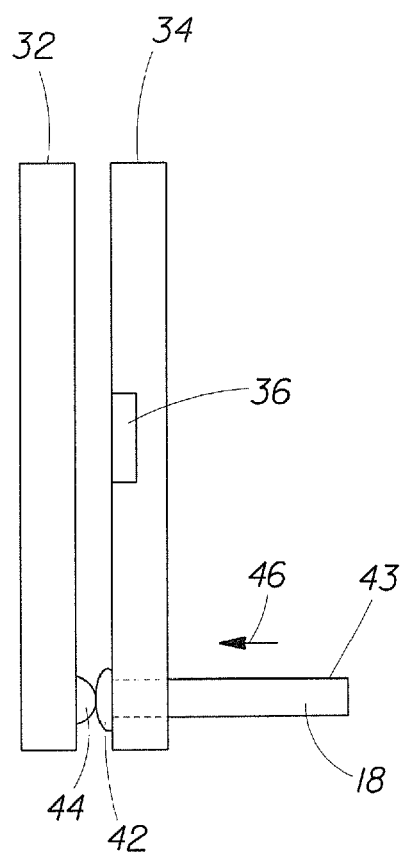
FIG. 4 is a side view of a cushion, support member and tuft of bristles of the toothbrush of FIG. 1.
Figure 5:
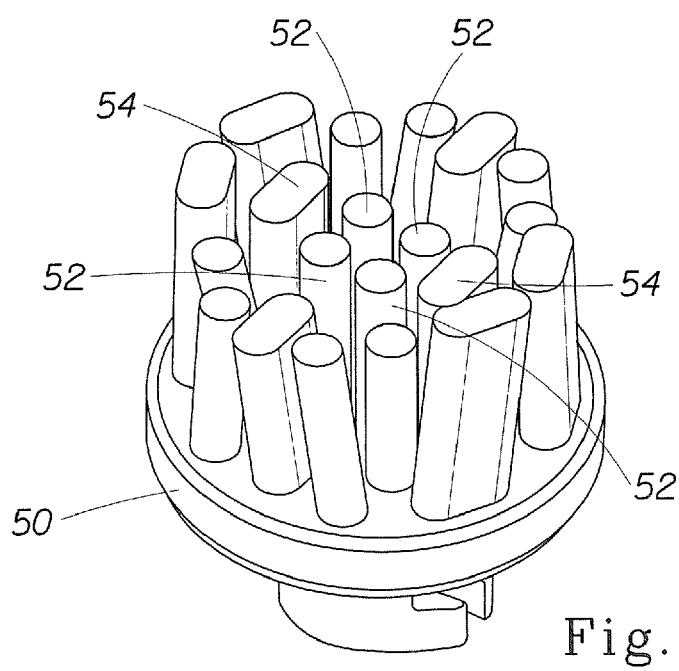
FIG. 5 is a perspective view of a second embodiment of a head for an electric toothbrush.
Figure 7:
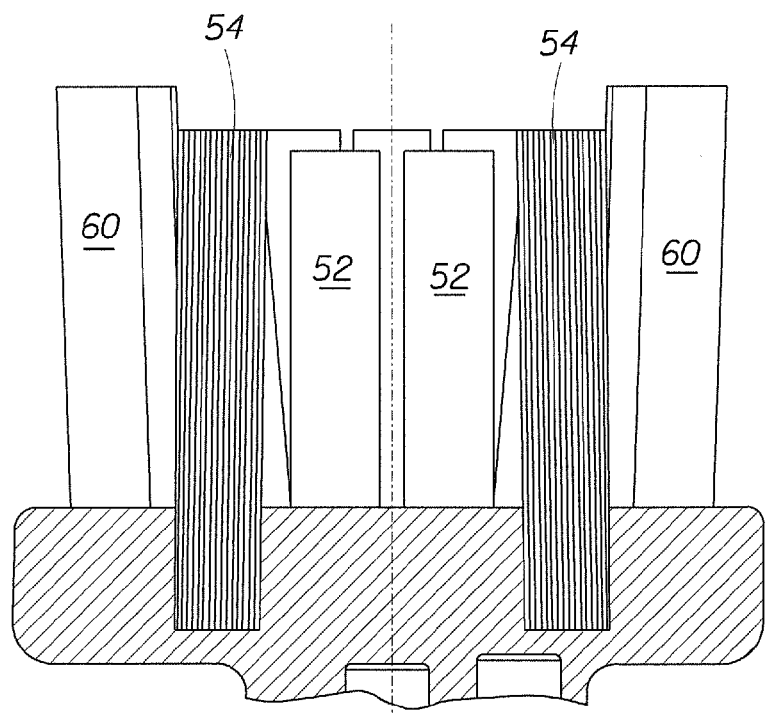
FIG. 7 is a sectional view of FIG. 6 taken along lines A-A.
Figure 6:
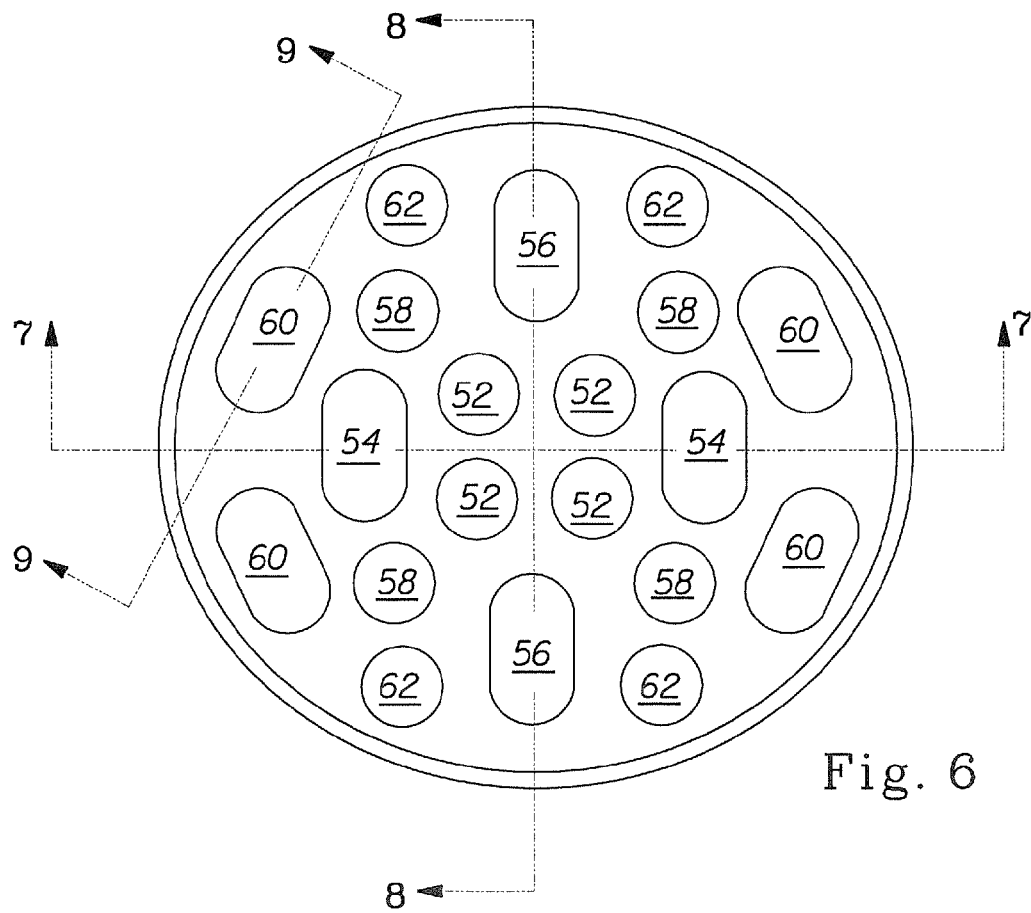
FIG. 6 is an enlarged top view of the head of FIG. 5.
Figure 8:
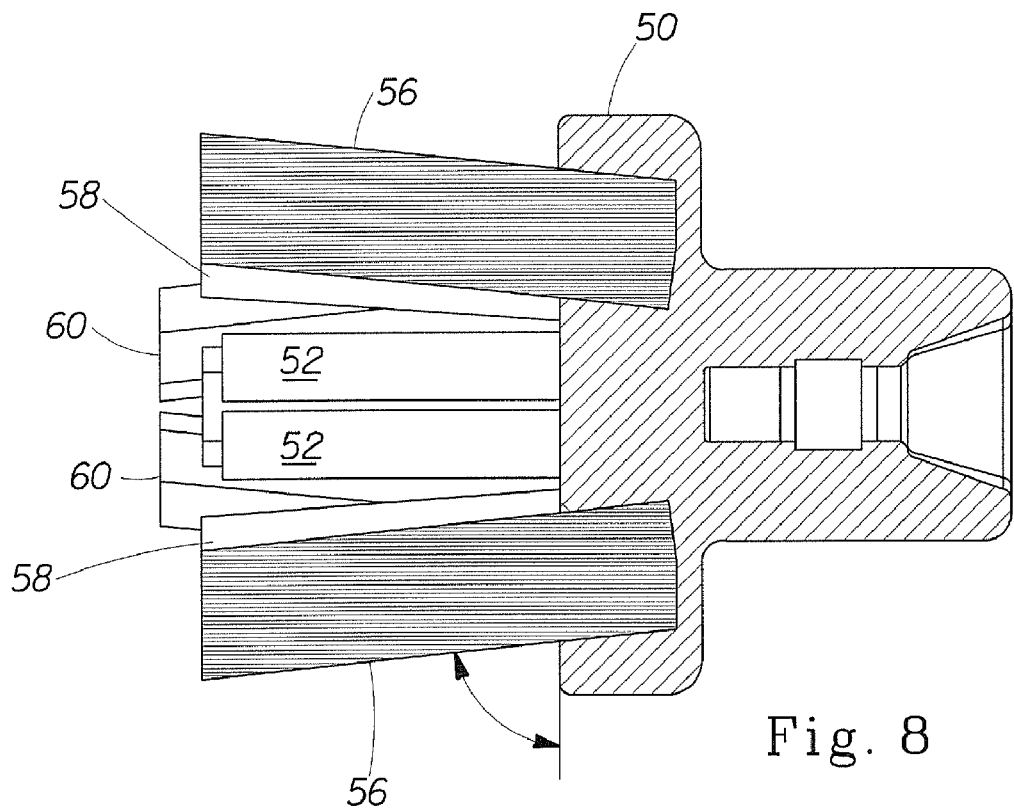
FIG. 8 is a sectional view of FIG. 6 taken along lines B-B.
Figure 9:
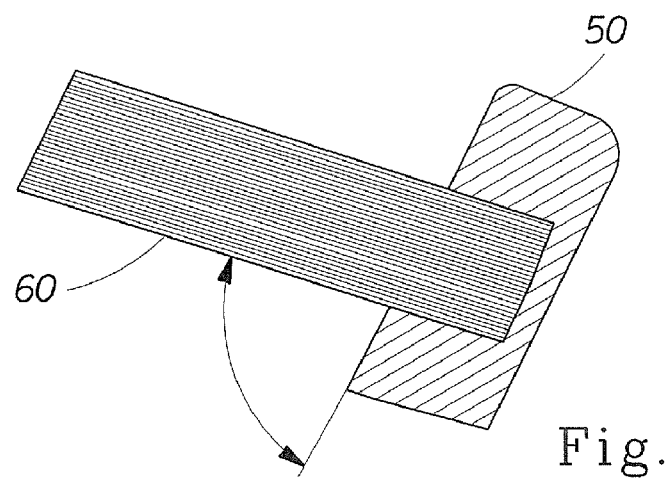
FIG. 9 is a sectional view of FIG. 6 taken along lines D-D.

Referring to FIG. 4, cushion 32 is shown adjacent support member 34. Only one of the tufts 18 is shown. The non-brushing end of tuft 18 has been melted into a mass 42. Mass 42 prevents tuft 18 from being withdrawn from its hole when a tensile force is applied to a brushing end 43 of the tuft along a long axis of the tuft. A cylindrically shaped protrusion 44 is provided on cushion 32 and is in contact with mass 42. At least one protrusion is provided for each tuft on the brush.

When a compressive force is applied to end 43 of tuft 18 along the long axis of the tuft, the tuft can move in its hole in a first direction 46 into the cushion. Such movement occurs because protrusion 44 acts like a spring, compressing under the force applied to it by mass 42. When the compressive force is removed the protrusion resumes its original shape, causing tuft 18 to move in its hole in a second direction substantially opposite the first direction. Such action assists in preventing damage to a person's gums in the event excessive pressure is used during brushing of the teeth.

Alternatively, mass 42 can be captured within support member 34 while the support member is being formed by injection molding (known as hot-tufting). In this case, cushion 32 is not required. In another alternative, member 34 is ultrasonically welded to base member 30 after the tufts are secured to member 34. As such, catches 36 and openings 38 are eliminated.

Embodiment 2

Turning now to FIGS. 5-9, a second embodiment of a head for an electric toothbrush will be described. A head (support member) 50 supports a multiplicity of tufts of bristles. The bristles all have a diameter of about 6 mil. Of course different filament diameters can be used (e.g. 6.0±0.5 mil).

A first group of tufts 52 have a round cross-section and extend perpendicular from head 50. Each tuft includes about 54 bristles per tuft. Tufts 52 rise about 7 mm above the head (the tufts' length) and preferably include bi-filament bristles. Such bristles are coextruded from two different materials, such as nylon 6.12 and nylon 6.10, and bend when exposed to water. All nylons mentioned for this embodiment are preferably polyamid. Further details on such bi-filament bristles can be found in PCT published application WO 98/14092.

A second group of tufts 54 are oval in shape (i.e. fin shaped) and also extend perpendicular from head 50. The filaments of this tuft are extruded from a single material such as nylon 6.12 Tufts 54 rise about 7.4 mm above the head. There are about 108 bristles in each tuft 54.

A third group of tufts 56 are also oval in shape and rise about 7.4 mm above head 50. Tufts 56 are preferably made of nylon 6.12 with each tuft including about 108 bristles. Tufts 56 are angled away from vertical by about 6 degrees in a radial direction away from the center of the head (see FIG. 8).

A fourth group of tufts 58 are round in cross-section and rise about 7.4 mm above head 50. Such bristles are coextruded from two different materials, such as nylon 6.12 and nylon 6.10, and bend when exposed to water. Each tuft includes about 54 bristles. Tufts 58 are angled away from vertical by about 7.5 degrees in a radial direction away from the center of the head (see FIG. 8).

A fifth group of tufts 60 are oval in cross-section and rise about 8.3 mm above head 50. Tufts 60 are preferably made of nylon 6.12 with each tuft including about 108 bristles. Tufts 60 are angled away from vertical by about 7.5 degrees in a tangential (i.e. circumferential) direction. Each tuft 60 is angled towards its closest neighboring tuft 60 (see FIG. 8) which makes the tufts more stable because the paired tufts support each other during brushing. This also assists in reducing bristle wear for these tufts.

A sixth and final group of tufts 62 are round in cross-section and rise about 7.4 mm above head 50. Tufts 62 are preferably made of nylon 6.12 with each tuft including about 54 bristles. Tufts 62 are angled away from vertical by about 6 degrees in a tangential (i.e. circumferential) direction. Each tuft 62 is angled towards its closest neighboring tuft 62 (see FIG. 5).

Endrounding of the bristles is accomplished after they are secured to the head. As such, the angle of tilt away from vertical for applicable tufts is limited to 7.5 degrees in order to obtain the best endrounding. Conventional stapling techniques can be used to secure the single tufts or segments to the head at an angle up to 7.5 degrees. If a tuft angle above 7.5 degrees is desired, an additional degree of freedom is required for the stapling tool (in this case, endrounding will not be as good).

Tufts 56 and 60 preferably include blue or green wear indicating bristles which are described in detail in U.S. Pat. No. 4,802,255. Oval shaped tufts 54, 56 and 60 are actually each made up of two groups of bristles. The oval shape increase the stiffness of these tufts and allows them to penetrate better between teeth than circular tufts. All of the oval shaped tufts have dimensions of about 1.45 mm by 2.9 mm All of the tufts with round cross-sections have a diameter of about 1.5 mm. The diameter of head 50 is about 13.25 mm. In an alternative embodiment, all of the tufts on the head range in length (the rise above the head) between about 6.7 mm to about 8.6 mm.

The invention has been described with reference to preferred embodiments. However, it will be appreciated that variations and modifications can be effected by a person of ordinary skill in the art without departing from the scope of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by referenced, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush comprising:
   a head having a planar front surface and a back surface;
   a base member;
   a support member fixed to the base member and having a plurality of holes extending therethrough;
   a resilient cushion member disposed, at least in part, between the base member and the support member, the cushion member having a plurality of protrusions extending therefrom; and
   a plurality of bristle tufts, each bristle tuft capable of engaging at least one protrusion;
   wherein at least a first bristle tuft is resiliently coupled to the head and extending from the front surface and through a corresponding hole in the support member in a first protruding direction; and
   at least a second bristle tuft resiliently coupled to the head and extending from the front surface and through a corresponding hole in the support member in a second protruding direction away from the first protruding direction,
   wherein applying a force to the first bristle tuft and/or the second bristle tuft causes the first bristle tuft and/or the second bristle tuft to deflect towards the back surface of the head.

2. The toothbrush of claim 1, comprising a plurality of round cross sectioned bristle tufts and a plurality of elongated cross sectioned bristle tufts.

3. The toothbrush of claim 2, wherein at least a portion of the plurality of elongate shaped cross sectioned bristle tufts are on the periphery of at least a portion of the plurality of round cross sectioned bristle tufts.

4. The toothbrush of claim 2, wherein at least a portion of the plurality of elongate shaped cross sectioned bristle tufts border an edge of the toothbrush.

5. The toothbrush of claim 4, wherein the front and back surfaces are outer surfaces.

6. The toothbrush of claim 1, wherein the second bristle tuft is disposed adjacent the first bristle tuft.

7. A toothbrush comprising:
   a head having a front surface and a back surface;
   a base member;
   a support member fixed to the base member and having a plurality of holes extending therethrough;
   a resilient cushion member disposed, at least in part, between the base member and the support member, the cushion member having a plurality of protrusions extending therefrom;
   at least one first bristle tuft extending from the first surface and through a corresponding hole in the support member at a first angle, the first surface being a planar surface; and
   at least one second bristle tuft extending from the first surface and through a corresponding hole in the support member at a second angle, wherein the first angle and the second angle are different;
   wherein the first and second bristle tufts are capable of engaging the plurality of protrusions such that the first and second bristle tufts are resiliently coupled to the head whereby applying a force to the resiliently coupled bristle tuft causes the resiliently coupled bristle tuft to move toward the head.

8. The toothbrush of claim 7, further comprising a third bristle tuft extending from the first surface at a third angle with respect to the head.

9. The toothbrush of claim 8, wherein the third bristle tuft is resiliently coupled to the head.

10. The toothbrush of claim 7, wherein the first bristle tuft is round and a plurality of second bristle tufts have an elongate shape cross section and at least partially surround the first bristle tuft.

11. The toothbrush of claim 7, wherein the second bristle tuft angles outward from an axis normal to the head.

* * * * *